US00PP25721P3

(12) United States Plant Patent
Egger

(10) Patent No.: US PP25,721 P3
(45) Date of Patent: Jul. 14, 2015

(54) ***X HEUCHERELLA* PLANT NAMED 'GLACIER FALLS'**

(50) Latin Name: ***X Heucherella* hybrid**
Varietal Denomination: Glacier Falls

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 184 days.

(21) Appl. No.: 13/987,659

(22) Filed: Aug. 20, 2013

(65) Prior Publication Data

US 2015/0059033 P1 Feb. 26, 2015

(51) Int. Cl.
*A01H 5/12* (2006.01)

(52) U.S. Cl.
USPC ..... Plt./441

(58) Field of Classification Search
USPC ..... Plt./441
See application file for complete search history.

*Primary Examiner* — June Hwu

(74) *Attorney, Agent, or Firm* — Klarquist Sparkman, LLP

(57) ABSTRACT

A new and distinct ×*Heucherella* plant substantially as shown and described, characterized by a vigorous, trailing habit, green leaves with a blue green cast as well as red to dark brown marks on the main veins, large, shallowly lobed leaves, and excellent vigor.

1 Drawing Sheet

Botanical denomination: ×*Heucherella* hybrid.
Variety designation: 'Glacier Falls'.

BACKGROUND OF THE INVENTION

The present invention relates to a new and distinct cultivar of ×*Heucherella* and given the cultivar name of 'Glacier Falls'. ×*Heucherella* is in the family Saxifragaceae. ×*Heucherella* 'Glacier Falls' originated from a controlled cross between a proprietary unreleased seedlings *Heuchera* V4, as the seed parent, and *Tiarella* massed proprietary trailing seedlings, as the pollen parent.

Compared to the seed parent *Heuchera* V4, the new cultivar is trailing rather than clumping.

Compared to the pollen parent, the *Tiarella* seedlings, the new cultivar has larger leaves that are broad rather than lobed and have a white veil rather than no veil.

Compared to ×*Heucherella* 'Sonic Smash' unpatented, (also with *Heuchera villosa* breeding lines) the new cultivar is trailing rather than clumping and has with leaves that that are shallowly lobed rather than lobed. The flowering stems are much shorter and fewer in number. The foliage of the new cultivar is more blue green in color.

This new ×*Heucherella* is unique in having the following characteristics:

1. a vigorous, trailing habit,
2. green leaves with a blue green cast as well as red to dark brown marks on the main veins,
3. large, shallowly lobed leaves, and
4. excellent vigor.

This new cultivar has been reproduced only by asexual propagation (division, cuttings, and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a 4 month old greenhouse grown ×*Heucherella* 'Glacier Falls' in a gallon container grown inside in an unheated greenhouse in April in Canby, Oreg.

FIG. 2 shows a 10 month old plant in the shaded field trail beds in October in Canby, Oreg.

DETAILED PLANT DESCRIPTION

The following is a detailed description of the new ×*Heucherella* cultivar based on observations of ten-month-old specimens growing in the field trials in shade in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on *The Royal Horticultural Society Colour Chart,* 5$^{th}$ edition.

Plant:

*Form*.—Basal rosette and trailing, herbaceous perennial.

*Hardiness*.—USDA Zone 4 to 9.

*Size*.—20 cm tall from top of the foliage to the ground and 72 cm wide.

*Habit*.—Low clumping and trailing.

*Vigor*.—Excellent.

*Roots*.—Fibrous, freely branching, fine, and white in color.

Stem:

*Size*.—Grows to 6 mm wide and 40 cm long.

*Surface texture*.—Glandular.

*Internode length.*—1 cm to 3 cm.
*Stem color*.—Greyed Purple 187A.

Leaf:
*Type*.—Simple.
*Arrangement*.—Rosette and alternate.
*Shape*.—Broadly ovate.
*Lobing/division.*—5 to 7 shallow palmate lobes.
*Venation*.—Palmate.
*Margins*.—Crenate.
*Apex*.—Mucronulate.
*Base*.—Cordate, lobes usually overlapping slightly.
*Blade size*.—Grows to 11 cm long and 11 cm wide.
*Surface texture*.—Glandular both surfaces.
*Petiole description*.—Grows to 10 cm long and 3 mm wide, glandular hairs, Yellow Green 145A in low light, Greyed Purple 187A in high light.
*Leaf color*.—Topside and bottom sides spring Yellow Green 146C with the speckled pattern Greyed Purple 183A; topside summer through winter Green N138B with pattern on the main veins Greyed Purple 187A, regular veins and leaf edges Green 137B, bottom side Green 138B.

Inflorescence:
*Size*.—Grows to 10 cm wide and 19 cm long.
*Type*.—Raceme.
*Number of flowers per raceme*.—About 200.
*Number of racemes*.—About 10.
*Peduncle*.—Grows to 25 cm tall, 2 mm wide at base, glandular hairs, Yellow Green 145A.
*Pedicel*.—Grows to 5 mm long, with glandular hairs, Greyed Red 182A to 182B.
*Bloom period*.—Late summer to fall in Canby, Oreg.

Flower bud:
*Size*.—2 mm wide and 3 mm long.
*Description*.—Glandular puberulent, ovoid.
*Color*.—White N155B.

Flower:
*Type*.—Perfect.
*Shape*.—Campanulate.
*Size*.—5 mm deep and 4 mm wide.
*Petal description*.—5 in number, narrowly oblanceolate, 3.8 mm long and 0.6 mm wide, tip acuminate, base attenuate, margin entire, glabrous and White NN155B on both sides.
*Calyx description*.—4 mm deep and 3 mm wide, with 5 lobes, divided ½ way to the base, campanulate, glandular hairs outside, glabrous inside, tip acute, margin entire, White NN155B.
*Stamen description*.—5 in number, filaments 4 mm long, White NN155A, anthers sterile, less than 1 mm, Orange Red N34.
*Pistil description*.—One central two beaked pistil, 5 mm long, White NN155A.
*Fragrance*.—None.
*Lastingness*.—Each raceme blooms for about 2 weeks on the plant.
*Flower attitude*.—Outwards.
*Flowering stem attitude*.—Semi-upright.

Fruit and seed: None.

Disease and pest tolerance: The new cultivar is typical to the genus. No known resistances to pests or diseases. No problems have been found in Canby, Oreg.

I claim:

1. A new and distinct ×*Heucherella* plant as herein illustrated and described.

* * * * *

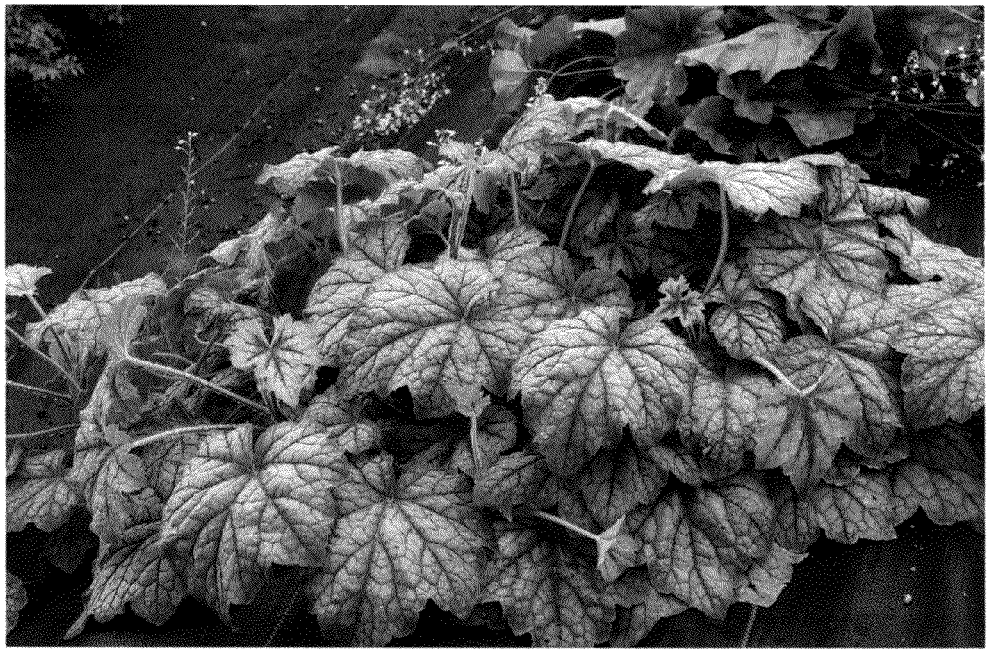

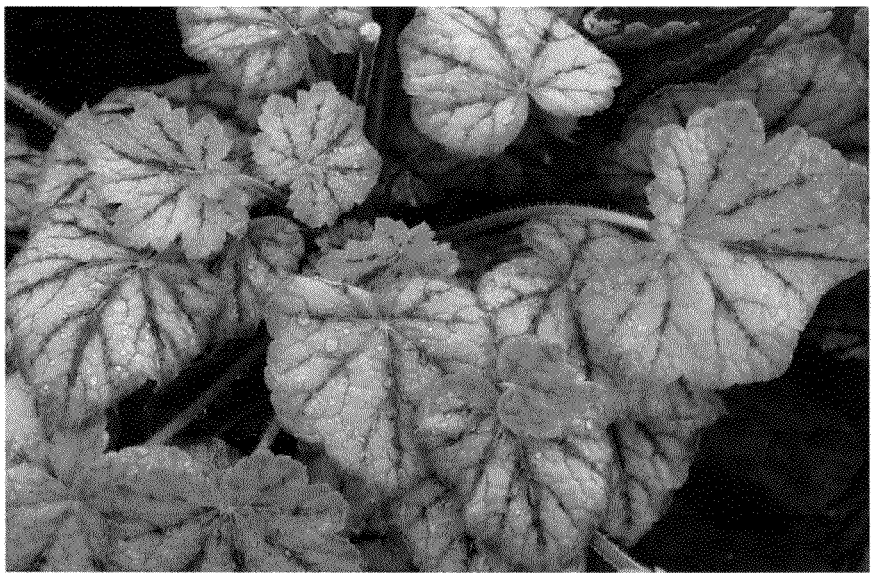
FIG. 1 above, FIG. 2 below